United States Patent [19]
Ron

[11] Patent Number: 5,647,834
[45] Date of Patent: Jul. 15, 1997

[54] SPEECH-BASED BIOFEEDBACK METHOD AND SYSTEM

[76] Inventor: Samuel Ron, 1, Sinai Street, Ramat Hasharon 47420, Israel

[21] Appl. No.: 497,253

[22] Filed: Jun. 30, 1995

[51] Int. Cl.$^6$ ............................... A61B 5/02; A61F 5/58
[52] U.S. Cl. .............................................. 600/23; 128/731
[58] Field of Search ..................... 128/731, 732, 128/898; 600/23, 27, 28

[56] References Cited

U.S. PATENT DOCUMENTS 4,685,448  8/1987  Shames et al. ........................... 600/23
5,441,047  8/1995  David et al. ......................... 128/904 X

FOREIGN PATENT DOCUMENTS 2102171  1/1983  United Kingdom ..................... 600/23

*Primary Examiner*—Lee S. Cohen
*Assistant Examiner*—Samuel Gilbert
*Attorney, Agent, or Firm*—Browdy and Neimark

[57] ABSTRACT

A method for effecting biofeedback regulation of at least one physiological variable characteristic of a subject's emotional state, comprising the steps of monitoring at least one speech parameter characteristic of the subject's emotional state so as to produce an indication signal, and using the indication signal to provide the subject with an indication of the at least one physiological variable. A system permits the method to be carried out in standalone mode or via the telephone line, in which case the indication signal may be derived at a location remote from the subject. Likewise, information relating to the subject's emotional state can be conveyed vocally to a remote party or textually through the Internet, and then processed as required.

39 Claims, 8 Drawing Sheets

SPEECH-BASED BIOFEEDBACK METHOD AND SYSTEM

FIELD OF INVENTION

This invention relates to biofeedback and in particular to a method and system for increasing or decreasing an involuntary or unconscious physiological process by self-regulating and exercising control over physiological variables and in particular speech.

BACKGROUND OF THE INVENTION

In this discussion of prior art, reference will be made to the following articles:

1. Holbrook A, Rolnick M L, and Bailey C W. *Treatment of vocal abuse disorders using a vocal intensity controller.* Journal of Speech and Hearing Disorders, 39:298–303, 1974.

2. Davis S M and Drichta C E. *Biofeedback Theory and Application in Allied Health.* Biofeedback and Self-Regulation, Vol. 5, No. 2, 1980.

3. Brody D M, Nelson B A, and Brody J F. *The use of visual feedback in establishing normal vocal intensity in two mildly retarded adults.* Journal of speech and hearing disorders, 40:502 507, 1975.

4. Roll D L. *Modification of nasal resonance in cleft palate children by informative feedback.* Journal of Applied Behavior Analysis, 6:397–403, 1973.

5. Stark R E. *The use of real-time visual displays of speech in the training of a profoundly deaf nonspeaking child: A case report.* Journal of Speech and Hearing Disorders, 36:397–409, 1971.

6. Guitar B. *Reduction of stuttering frequency using analog electromyographic feedback.* Journal of Speech and Hearing Research, 18:672–685, 1975.

7. Hison T J. *Respiratory function in speech.* In F D Minifie, T J Hison and F Williams (Eds), *Normal Aspects of Speech, Hearing and Language,* Prentice-Hall, Englewood Cliffs, N.J., 1973.

8. Stassen H H, Bomben G, Gunther E. *Speech characteristics in depression.* Psychopathology, 24:88–105, 1991.

9. Murray I R, Arnott J L. *Toward the simulation of emotion in synthetic speech: A review of the literature on human vocal emotion.* Journal of Acoustical Society of America, 93:1097 1108, 1993.

10. Brenner M, Dohersy T, Shipp T. *Speech measures indicating workload demand,* Aviation Space and Environmental Medicine, 65:21 26, 1994.

Biofeedback may be defined as the technique of using equipment (usually electronic) to reveal to human beings some of their internal physiological events, normal and abnormal, in the form of visual and auditory signals in order to teach them to manipulate these otherwise involuntary or unfelt events (such as heart beat and emotions) by manipulating the displayed signals. This technique allows an open feedback loop to be closed by a person's volition so as to modify the outcome based on preset goals. To achieve such goals requires voluntary cooperation on the part of the subject. Psychologically, the functions to be controlled are associated with the structures that determine the emotional status of the organism.

Various types of devices have been developed and used in biofeedback systems in which one or more signals representative of physiological variables are fed back. These variables constitute, for example, muscle activity, galvanic skin resistance, heart rate, temperature or blood pressure. In the prior art, appropriate transducers have been used for transforming these signals to visual or audio stimuli. The subject is expected to control mentally one or more of the monitored physiological functions, thus modifying the outcome of the physiological variables.

Emotional feeling is considered basically a perception of bodily changes and reflected through measurements in the autonomic changes. Some of the measurements are considered to indicate generalized stress or arousal rather than particular emotions. It is known to use biofeedback for training subjects in relaxation techniques by measuring stress-related variables such as pulse rate, breathing pattern, blood pressure, temperature and the electrical resistance (galvanic skin resistance) of the palm of the hand or its fingers.

The response of an individual to a verbal provocation which touches him personally is usually related to an emotional reaction with some degree of stress. If, for example, a person tells a lie, this will result in a specific physiological reaction whose comparison to the complementary response when no lie is told may be indicative of a lie having been told. However, whilst a particular emotional state related to stress will always produce a similar physiological change, it is not possible to infer the cause of such stress merely from the fact of such a physiological change. Thus, prior art in the field of biofeedback which aims to manipulate an emotional state, is confined mainly to the aspects of arousal and relaxation.

Spector (U.S. Pat. No. 5,209,494) discloses a biofeedback system which monitors an involuntary physiological function of an individual and indicate the individual's-state of stress, making it possible for the individual to exercise control over the function being monitored. Stress is measured using a temperature sensor device.

Agoston (U.S. Pat. No. 4,184,485) discloses a measuring arrangement for decreasing the emotional influence on instrumental diagnostic measurements using heart rate in a biofeedback system in which the change of a subject's emotional state is indicated by changing the tone pitch of an audio output heard by the subject or by showing the pulse rate on a digital readout indicator.

Shiga (U.S. Pat. No. 4,345,505) discloses a self-training biofeedback system in which the electrical activity of a subject's brain is used to indicate his state of relaxation, and a binary count output system is employed for indicating the relaxation period.

Bittman (U.S. Pat. No. 5,343,871) teaches the use of an apparatus for mediating a biofeedback session with a human subject in which the clarity of an image and sound improve as an indication of success the subject in reaching a state of relaxation.

Dardik (U.S. Pat. No. 5,163,439) teaches the use of biofeedback for enabling a subject to control his pulse rate, thus learning to relax and thereby reduce tension and its physiological consequences.

The applications of biofeedback techniques using speech as the physiological variable to be fed back and controlled has been used in the area of speech pathologies in controlling vocal intensity, resonance, and pitch. However, it has been used very little in teaching patients with hearing deficits to speak with proper articulation and expressing emotion. Speech is an overlaid function: there is no specific organ for speech. Instead, anatomical structures of the aerodigestive tract must function in a coordinated manner to produce intelligible sound. Normal speech production requires the coordinated activity of the respiratory muscles and those muscles responsible for phonetics-and articulation. A controlled delivery of air in expiration is needed to allow the muscles of the larynx and oral pharynx to modulate the vibrations we interpret as voice. This is a process that necessarily involves the precise control of muscular functions. As a result, any aberrant muscle activity would naturally cause, or contribute to, many types of speech modifications.

It is well known that emotion and stress (a psychological state which is accompanied by the specific emotions of anxiety, fear and/or anger) modify the speech so that the changes are recognizable by other people. Sentences as "you sound sad" or "you sound angry" are clearly indicative that a person's voice reflect his emotional state. Among the speech characteristics, the fundamental frequency ($F_0$) is an important variable that changes when there is an emotional change and varies between different emotions. Several others speech characteristics are considered to be important in the analysis of emotion from speech (Stassen et al.[8]). Such characteristics include speech flow (the speed at which utterances are produced as well as the number and duration of temporary breaks in speaking); loudness (the amount of energy used to articulate utterances, and the speaker's dynamic expressiveness); intonation (the manner of producing utterances with respect to rise and fall in pitch); mean utterance duration and variability of utterance duration; mean pause duration and variability of pause duration.

Murray et al.[9] reviewed the state of the art in our understanding of human vocal emotion. The acoustic properties appearing to be among the most sensitive indicators of emotion were attributes that specified the contours of $F_0$ throughout an utterance. Murray et al.[9] refer to a multivariable model in which different speech characteristics are associated with emotions such as anger, happiness, sadness, fear, and disgust. For example, the emotion of anger is expressed in faster speech rate, higher pitch average, wider pitch, higher intensity, abrupt pitch changes and tense articulation.

Brenner et al.[10] show that stress in speech can be detected using speech rate, pitch, vocal intensity and derived speech measure (z-scores).

Holbrook et al.[1] discloses an instrument for controlling voice intensity in a treatment program for patients with dysphonia (i.e. roughness of sound) related to vocal cord lesion and to laryngeal hypertension. The instrument provides auditory feedback contingent on excessive vocal intensity.

As reported by Davis et al.[2], Brody et el.[3] use a vocal-activated relay to provide visual feedback of vocal amplitude for subjects who habitually used very soft voices. Subjects demonstrate significant increases in their use of normal voice intensity.

As reported by Davis et al.[2], Roll[4] utilizes a biofeedback approach in patients who suffer from hypernasal speech (an excessive undesirable amount of perceived nasal cavity resonance that occurs during the phonation of vowels). The resonance characteristics of vowels sounds are treated as operant behaviors. Differential feedback is arranged for nasal versus non-nasal responses, so as to display a visual indication when the nasal vibration exceeds an arbitrary unit, thereby teaching patients to control their nasal vibration.

Stark[5] reports the use of real-time amplitude contours and spectral display of speech in the training of speech-production skills.

The development of electromyographic (EMG) biofeedback as a means of measuring, recording, and displaying the electrical activity of living muscle has significant implications for the assessment and treatment of communication disorders. EMG recording provides a more objective means of measuring and characterizing the nature of muscle activity during speech, typically focused on few muscle groups.

Most prior studies limit their observation to a single level of the speech mechanism such as the laryngeal (in stuttering and dysarthria as done by Guitar[6]) or respiratory muscles (Hison[7]) both reported by Davis et al.[2]. The use of biofeedback in teaching communication disorders introduces a quantitative measure to the improvement of the speech. However, qualities of speech such as emotion have not been treated by biofeedback.

It is well known that when subjects are tired, speech characteristics are affected. Speech in a tired subject has a lower speech flow, a slower pitch, a lower intensity, a lower derived speech measure, a lower intonation, a larger mean pause duration and a larger variability of mean pause duration. Nevertheless, speech fatigue has not been proposed either as a criterion for finding a subject's fatigue level so as to determine his or her mental state, or as a means to avoid treating subjects who are tired.

SUMMARY OF THE INVENTION

It is a principal object of the invention to provide a method for using speech characteristics in a self-training biofeedback system. Depending on the subject's mental state, speech characteristics change and are a sensitive measure of the subject's emotional state. The invention offers a method by which a subject can learn to control or modify his speech characteristics by bringing his mind into a required emotional state.

According to a first aspect of the invention there is provided a method for effecting biofeedback regulation of at least one physiological variable characteristic of a subject's emotional state, comprising the steps of:

(a) monitoring at least one speech parameter characteristic of the subject's emotional state so as to produce an indication signal representative of the at least one physiological variable, and (b) consciously altering the subject's emotional state so as to induce a desired change in the indication signal.

In accordance with a further aspect of the invention, the method is carried out over the telephone and the subject is not physically connected to any wires.

A system in accordance with the invention offers sets of pre-recorded and stored audio-visual scenarios in sequences of varying levels, in which a subject can move from one scenario to the next after he has reached a required level of control of the relevant emotion. The system provides a real time interactive multimedia system, which is not restricted to the prior art presentation of "clinical" images such as, for example, biographs; the presentation of instantaneous changes in the measured variables as a continuous record in X-Y format; or the use of acoustic tones and audio beat-frequencies to indicate to the subject the value of the parameters being monitored. Specifically, the interactive audio-visual stimuli used in the present invention allow for the presentation of more emotionally-related variables within a more interesting, tailor-made environment which is thus more conducive for self-training. Moreover, since no other physiological variable is so indicative of emotion as speech, the invention provides a much more accurate indication of a subject's emotional state than hitherto proposed approaches.

It is a further object of the invention to provide a method and system for using primarily the emotion in speech as the operant of the fed back signal. The emotional state of the subject has its own specific speech characteristics which change depending on the subject's psychological state. The subject can learn to control his emotion by controlling his speech, or if he lacks the knowledge how to express himself, he can learn to do so.

When a subject is relaxed, the pitch of his voice is lower than when he is under stress. Thus, as a first approximation, the subject can be shown, for example, an animation in which motion depends on the change in the pitch; or, for example a cartoon whose size depends on the pitch. For a more accurate representation of the emotional state, several speech characteristics are used in a model of the fed back signal to drive the audio-visual stimuli.

Yet a further object of the invention is to allow analysis of a subject's emotional state to be conducted and conveyed to a remote party via a communication channel. The communication channel can be a telephone line permitting remote analysis of the subject's speech so as to determine the his emotional state. Alternatively, the analysis can be performed locally and encoded within a file which is then communicated to the remote party.

Other objects and advantages of the invention will become apparent from the following detailed description of several preferred embodiments.

BRIEF DESCRIPTION OF THE DRAWINGS

In order to understand the invention and to see how the same may be carried out in practice, some preferred embodiments will now be described, by way of non-limiting example only, with reference to the accompanying drawings, in which:

FIG. 2b shows schematically a control unit for use with the system shown in FIG. 2a;

DETAILED DESCRIPTION OF PREFERRED EMBODIMENTS

Figure 1:
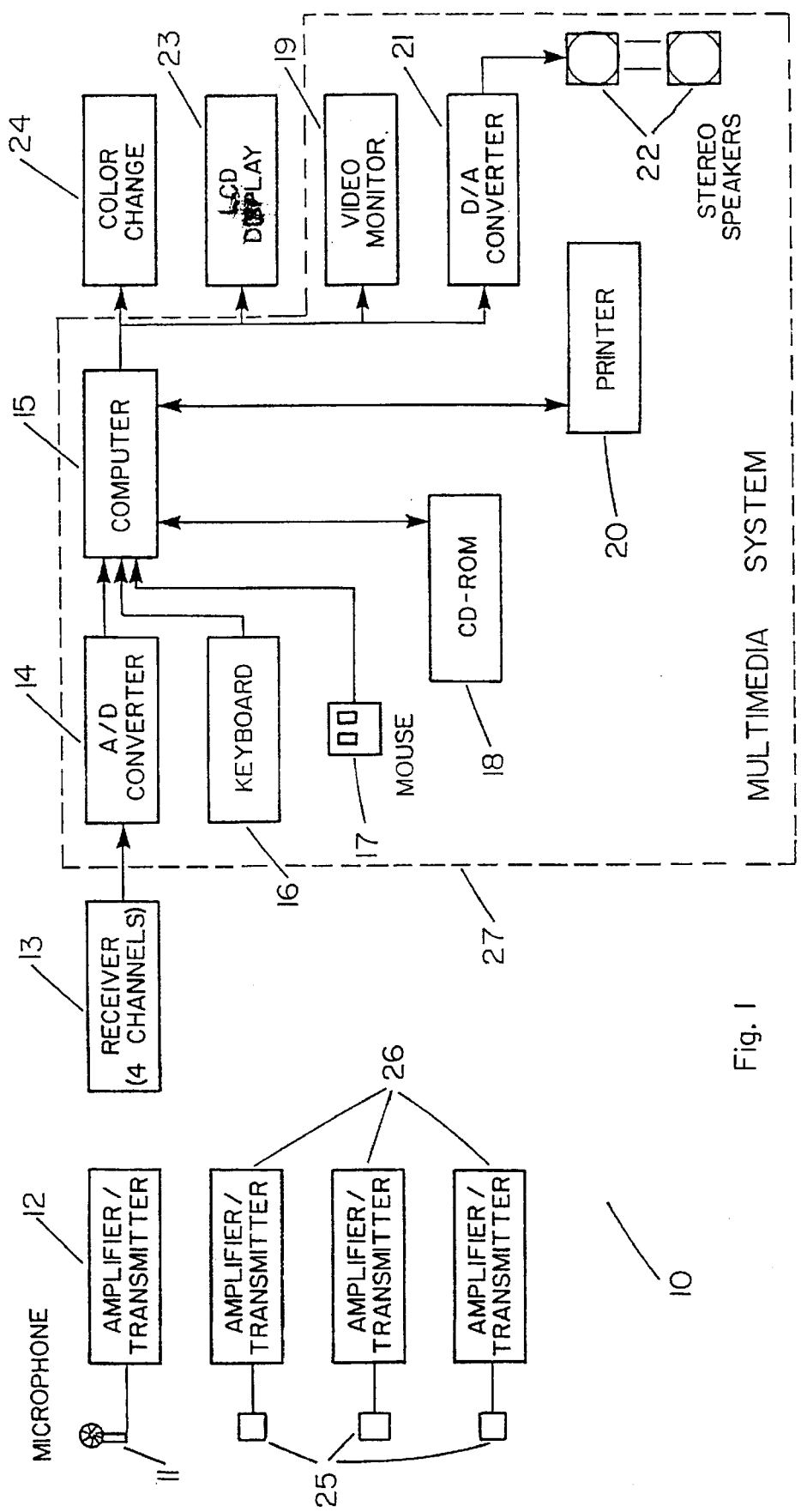
FIG. 1 shows schematically a biofeedback system which uses speech characteristics and physiological signals as the fed back signals.

FIG. 1 illustrates a system 10 for providing visual images and auditory signals related to emotional speech feedback and other physiological signals. The system 10 comprises a microphone 11 for picking up a speech signal and transmitting it via an infrared transmitter 12 to an infrared receiver 13. An Analog-to-Digital (A/D) converter 14 is coupled to the infrared receiver 13 for digitizing the analog signal received thereby and feeding it to a computer 15. The computer 15 includes a hard disk (not shown) and has on board hardware such as a DSP (Digital Signal Processor) (not shown) which partially constitutes a speech analyzer system for speeding up the process of detecting those characteristics which are sensitive to, and indicative of, changes in the emotional state of the subject. The computer 15 is programmed to derive speech characteristics from the digitized speech signal. The manner in which this is done is not itself a feature of the invention and is well known in the art. For example, Murray et al.[9] make reference to various techniques for deriving speech characteristics from a digitized speech signal.

Coupled to the computer 15 is a keyboard 16, a mouse 17, a CD-ROM 18, a video display device 19 and a printer 20. Also coupled to the computer 15 is a digital to analog (D/A) converter 21 to which a pair of stereo loudspeakers 22 are connected, an LCD graphic display 23 and a color change unit 24. The video display device 19 is responsive to the computer 15 for displaying menu options during the feedback training, and the speakers 21 are responsive to the computer 15 for generating music, sounds or pre-recorded verbal instructions which are synchronized with the visual images. The computer 15 may further be programmed so as to present any desired visual image on the video display device 19 such that the visual image presented to the subject varies in accordance with his or her emotional state.

The computer 15 includes a hard disk and a digital signal processor (DSP) (not shown) for performing speech analysis and detection of the characteristics which are sensitive to, and represent changes in, the emotional state of the subject. Alternatively, where speed is not critical, the DSP may be dispensed with and the algorithms can be implemented in software. The computer 15 operates under the control of the keyboard 16 and the mouse 17 so as to permit the subject to choose the visual image and the auditory signal from a large repertoire stored in the CD-ROM 18.

A given scenario cannot always be associated with the emotional topic to which the scenario is believed to be related as it is well known that what might be a relaxing scenario for one subject could be a stressful scenario for another. Using the keyboard 16 the subject can choose from preset scenarios that are associated with a specific emotion such as of relaxation, stress, anger, happiness, sadness, fear, and disgust.

In practice, the subject can choose auditory sounds independent of the displayed visual images but, by default, the speakers 22 are adapted to reproduce auditory sounds considered by most subjects to have the same emotional effect as a displayed visual image. The subject's personal data, a description of the displayed visual image and any statistical data descriptive of the success or failure of the subject can be printed on the printer 20.

The visual display can be reproduced graphically on the LCD graphic display 23 or can be represented in an analog form by the color change unit 24 which is adapted to change colors depending on speech characteristics or on emotional change as detected by one of the sensors. For example, the color change unit 24 may produce a blue display if the subject is relaxed when speaking, and change to red when he is sad. By such means the subject's emotional state as reflected by his speech is immediately visibly apparent to the subject. A plurality of different sensors 25 for detecting heart rate, galvanic skin resistance, and so on, are coupled to respective infrared transmitters 26 which amplify the signals generated by the sensors 25 and produce infrared signals which, in turn, are transmitted to the receiver 13 which is able to handle four signals simultaneously.

The A/D converter 14, the computer 15 as well as the keyboard 16, mouse 17, CD-ROM 18, video monitor 19, printer 20, D/A converter 21 and loudspeakers 22 may be realized by a commercially available multimedia system 27. The extent of the invention is then limited by the skill and imagination of the multimedia system programmer. For example, animation effects can be displayed on the display monitor whose content (foreground and/or background) varies according to the subject's measured emotional states. For example, a landscape scene can be displayed which is bright and sunny when the subject is happy, but changes to dark and cloudy when he is sad. A thunderstorm can be animated to represent anger and other animation effects can be employed to represent different emotions as required.

In order to allow for the fact that some people cannot speak emotionally, the system provides an option to record other physiological variables sensitive to emotions such as heart rate galvanic skin resistance and temperature. By such means, a subject can be trained to visualize through visual images and to hear the audio signals so that he can either attempt to increase his emotion or to control it. Once the subject is aware how these emotions can be changed, he switches to speech and by generating the similar feelings as before he learns to change the speech characteristics so that these feelings will effect similar changes to the visual imagery as were originally produced.

For example, while some audio-visual signals can evoke fear, the subject can feel fear or anxiety as interpreted from heart rate changes. However, his speech characteristic might not show the typical moderate increase in pitch associated with anxiety but, rather, a much faster speech rate associated with fear. The subject can learn to control his fears, thereby reducing his heart rate and thus changing the content, wholly or partially, of the audio-visual scenario to a relaxed one. Alternatively, the subject can, by changing his voice, modify the audio-visual scenario so as to reflect fear, if he so wishes.

According to another embodiment, a subject may be asked to assume a more relaxed state, resulting in his speech profile having a lower pitch, a lower rate, a lower vocal intensity and a lower derived speech measure. Success in training also has therapeutic values to teach patients who have difficulty in expressing emotion in their conversation how to change their speech characteristics. The learning process has a general effect of mastering emotional control.

The system 10 can also be used in the form of a game wherein the object is for a subject to assume a desired emotional state such as being relaxed or excited. To win or "score" in the game, the subject has to change his speech characteristics so that they reflect the desired emotional state. The goal of such a game could be for example, to teach a player to experience a particular emotion and to proceed with the game only when the desired emotion is correctly represented in his speech characteristics.

The game operates by displaying visually a desired scenario on the video monitor 19. The player must then relate a story corresponding to the displayed image so that his speech characteristics truly reflect the nature of the image. For example, if the scenario is "scary", his voice should express fear, whereas a sad story should be read with a sad voice. The "score" is based on the change in the player's speech characteristics. Several different emotional responses as well as skill levels may be associated with the scenario so that the player can develop various speech characteristics each corresponding to a respective emotion. Once the player has completed a scenario, he can move to another scenario which represents a different emotion. The game is both entertaining and enhances the ability of the player to exercise control over his emotional expression in speech. Another illustrative example is a racing game in which in an animated image of two people walking fast is shown. The speed of one subject is determined by the computer 15 whilst that of the other subject is determined by the emotion the subject is asked to express in his voice.

Figure 2A:
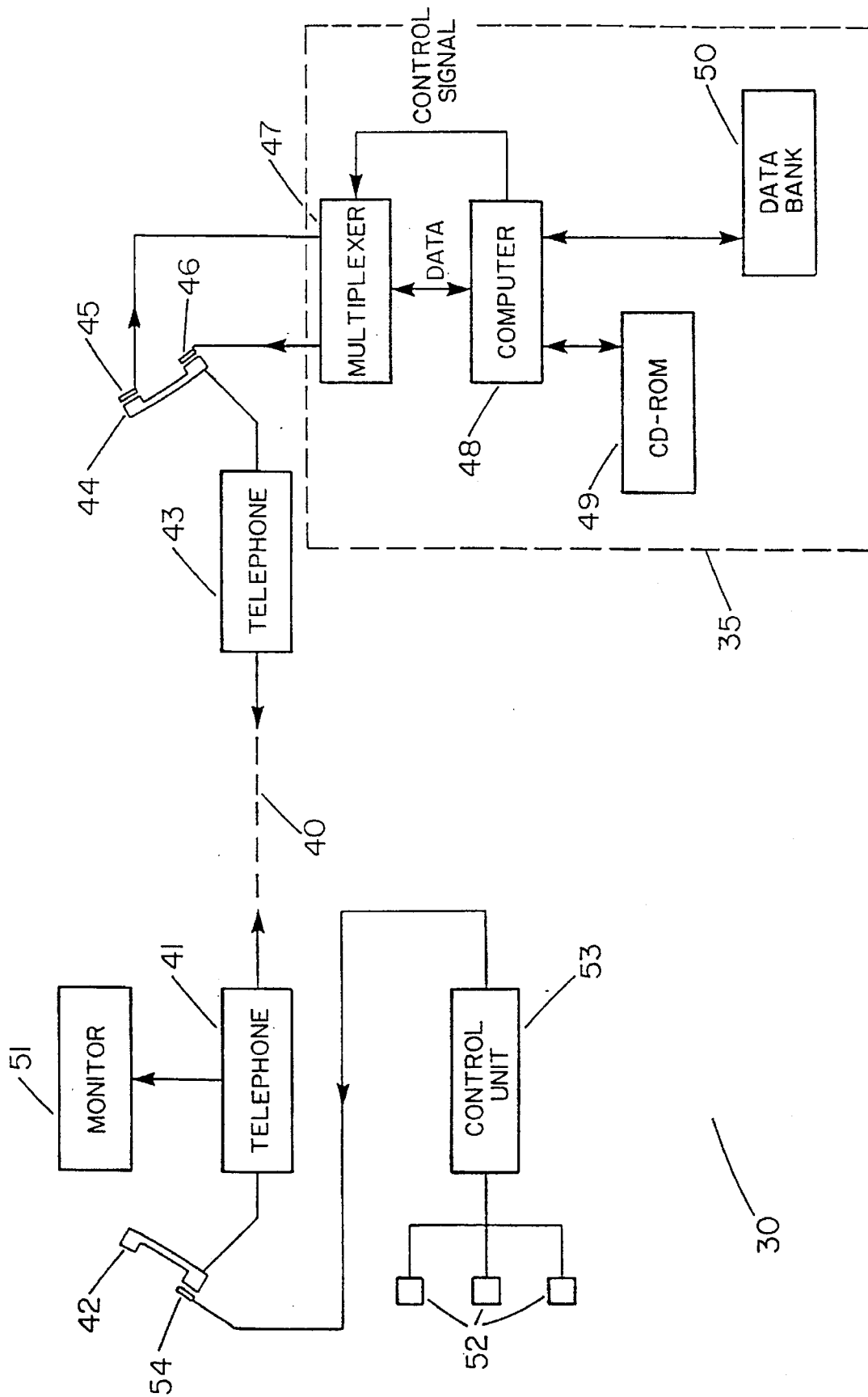
FIG. 2a shows schematically a manned biofeedback system operating through a telephone for allowing remote interactive monitoring and analysis of a subject's speech characteristics.

Referring to FIG. 2a there is shown a block diagram of a system 30 which allows a subject to speak to a remotely placed biofeedback system, shown generally as 35, via a telephone line 40. The system 30 does not need any special installation or permission to use the telephone system, since the telephone line 40 and the two end-systems connected thereto require no modification. A telephone 41 has a handle 42 and is coupled, via the telephone line 40, to a remote telephone 43 having a handle 44 housing a microphone 45 and an earpiece 46. A voice signal is picked up by the microphone 45 and conveyed to a multiplexer 47. The multiplexer 47 multiplexes the incoming voice and the fed back signal to the earpiece 46. The multiplexer 47 is controlled by a computer 48 which also analyses the voice data. If desired, the telephone 43 can be connected directly to the multiplexer 47 instead of via the handle 44. A CD-ROM 49 is coupled to the computer 48 for storing therein the scenarios and the audio messages whilst speech characteristics, subject data from previous sessions and any relevant information are stored in a data bank 50 also connected to the computer 48.

The signal from the analyzed speech used for biofeedback through the microphone 46 can be heard by the subject with the telephone handle 41. The sound heard by the subject can be, for example, in the form of a tone of short 200 ms bursts whose frequency changes based on the emotional state of the subject. Alternatively, a phrase may be presented to the subject indicative of his emotional state. Such pre-recorded evaluations as well as instructions as to how to proceed with the training can be dictated to the subject from the information within the CD-ROM 49. A display monitor 51 is coupled to the telephone 41 for displaying the fed back signal visually. The display monitor 51 may be provided as an integral component of a video-telephone system. The displayed image can be in the form of an animation sequence whose frames are displayed at a variable frequency dependent on the subject's speech characteristics. Alternatively, conventional graphical representations of biofeedback images such as heart rate, temperature, blood pressure etc. may be displayed on the display monitor 51.

The subject is instructed that in order to reduce his anger he should aim at reducing the rate of the burst, or should aim at a lower tone. According to one embodiment, when the subject is angry the rate of the burst is one per second (or a tone at 3000 Hz), whereas when the subject is relaxed the rate is reduced to one burst every three seconds (or 500 Hz). By such means, the subject can receive the fed back signal through the same telephone 41 through which he speaks. It is possible, if so desired, to store the progressive training lessons to be shown to the subject in the CD-ROM 49 and the results of the course of training lessons can be stored in the data bank 50, so as to allow any improvement in the subject's response to be relayed at the end of the training course.

For some subjects, the speech might not reflect the emotional state as the subject may be excited but his speech be monotonous with low pitch indicating a relaxed state.

Such subjects may either not be aware of their emotional state as reflected in the physiological measurements, or they might not know how to speech emotionally. To train such subjects, there are provided a plurality of sensors 52 coupled to a control unit 53 which, in turn, is connected to a supplementary microphone 54 fitted to the telephone 42. The sensors 52 measure such variables as heart rate, galvanic skin resistance or temperature, known to be influenced by emotional state. The control unit 53 feeds the microphone 54 with short bursts that transmit the measured physiological information to the computer 48 which analyses the speech.

When the system 30 is used to measure physiological variables in addition to speech, the training starts when the subject speaks and one or two physiological variables are measured simultaneously. If, for example the subject is under stress as indicated by the galvanic skin resistance but the analysis of his speech does not reveal it, the subject is told that he does not express his emotions. Depending on the task, the subject can be encouraged either to lower his stress by giving him the galvanic skin resistance as the fed back signal, or be given a fed back signal correlated with the emotional state of his speech characteristics and asked to increase his emotional reaction.

The subject is presented with a short intermittent burst of constant frequency tones and asked to lower the tone frequency by decreasing his stress (when the fed back signal is based on the galvanic skin resistance), or to increase the tone frequency of the fed back signal by increasing his stress (if the fed back signal is based on speech characteristics). The computer 48 may easily be programmed to distinguish the data derived from the physiological variables from the speech data, thus analyzing each data component separately. The intermittent tone burst can be made at a rate of every several seconds for a period of 200 ms, thus not interfering for long periods with the subject's speech pattern transmission. By default, the short bursts are heard by the subject. If it is desired to prevent the subject hearing the burst, the output signal from the telephone 42 and from the control unit 53 may be alternately connected to the telephone line via a multiplexer. Such a configuration is described below with reference to FIG. 2c of the drawings.

Figure 2B:
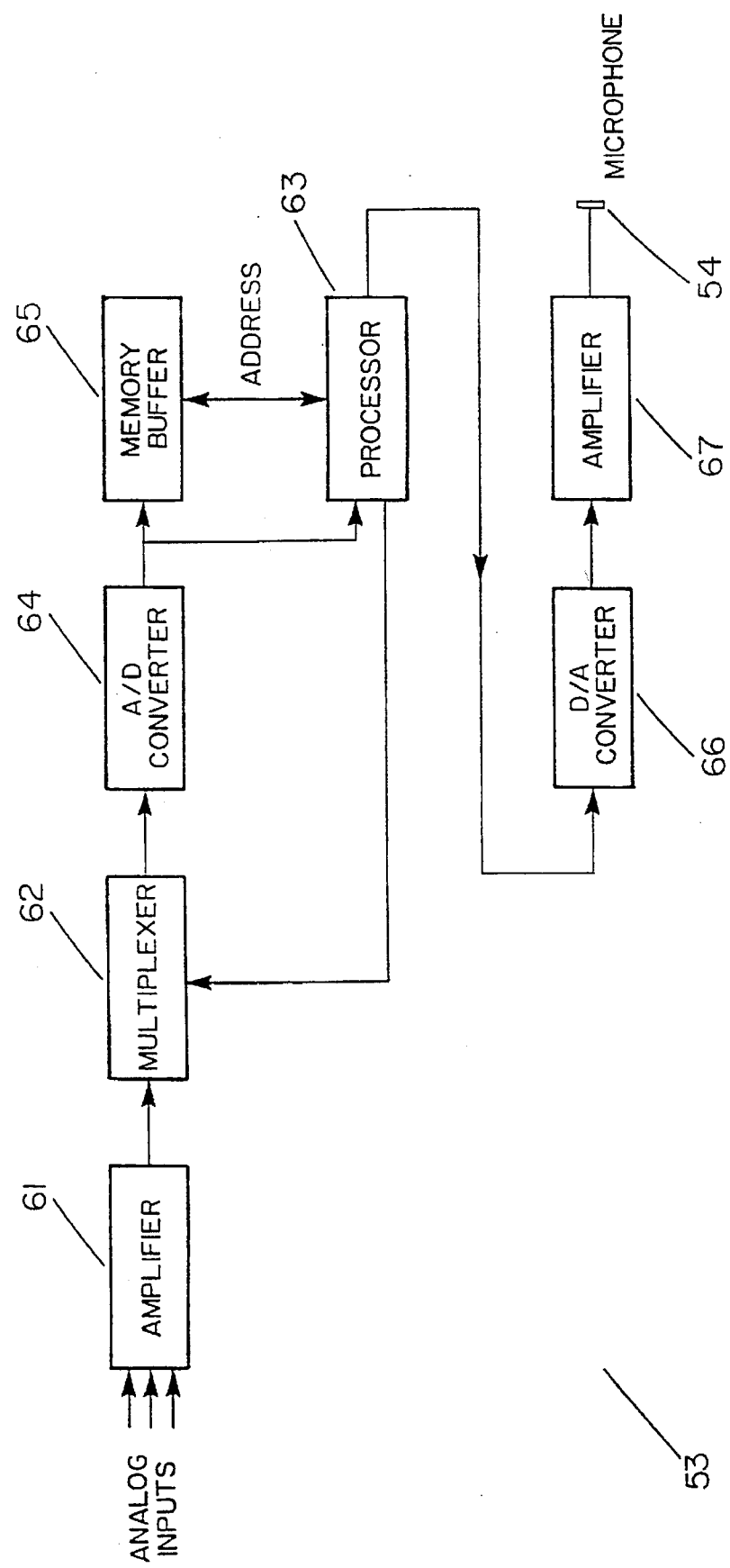

FIG. 2b shows a block diagram of the control unit 53 shown functionally in FIG. 2a to which further reference is made in the following description. The signals produced by the sensors 52 are amplified by an amplifier 61, multiplexed by a multiplexer 62 which is controlled by a processor 63. The multiplexed data from the multiplexer 62 is digitized by an analog to digital (A/D) convertor 64 and the data is then fed to the processor 63 and to a buffer memory 65. The function of the buffer memory 65 is to maintain the data in the buffer for a duration long enough to be processed by the processor 63, after which the buffer is updated with new data. The processed data is converted to an analog signal by the D/A converter 66, amplified by an amplifier 67 and fed to the microphone 54 within the handle 41 of the telephone 42. Thus the signals are transmitted through the telephone 42 to a remotely located biofeedback system.

Figure 2C:
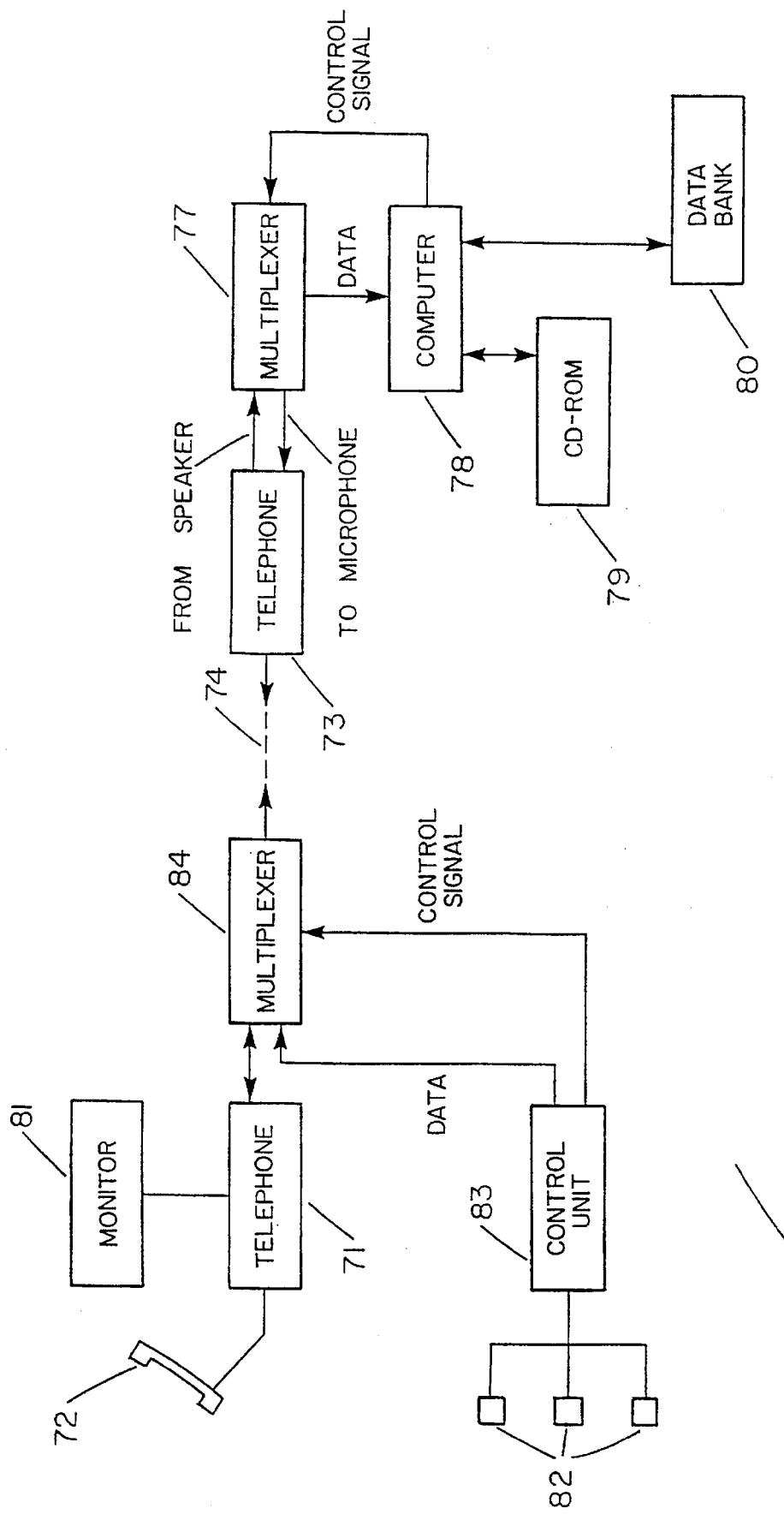
FIG. 2c shows schematically an unmanned biofeedback system operating through a telephone for allowing self-monitoring of a subject's speech characteristics.

FIG. 2c illustrates a block diagram of a system depicted generally as 70 similar to the system 30 described above with reference to FIG. 2a of the drawings, but allowing for self-monitoring of a subject by means of a telephone via a remote biofeedback system.

The system 70 comprises a telephone 71 having a handle 72 and being coupled to a remote telephone 73 via a telephone line 74. The telephone 73 houses a conventional microphone and earpiece (not shown), both of which are connected, via a multiplexer 77, to a computer 78 which analyses the voice data. A CD-ROM 79 is coupled to the computer 78 for storing therein the scenarios and the audio messages, whilst speech characteristics, subject data from previous sessions and any relevant information are stored in a data bank 80 also connected to the computer 78.

The signal from the analyzed speech used for biofeedback is fed through the microphone to the telephone 73 whence it is transmitted as a voice signal down the telephone line 74 and is heard by the subject through the earpiece in the handle 72 of the telephone 71. The sound heard by the subject can be, for example, in the form of a tone of short 200 ms bursts whose frequency changes based on the emotional state of the subject. Alternatively, a phrase may be presented to the subject indicative of his emotional state. Such pre-recorded evaluations as well as instructions as to how to proceed with the training can be dictated to the subject from the information within the CD-ROM 79. A display monitor 81 is coupled to the telephone 71 for displaying the fed back signal visually. The display monitor 81 may be provided as an integral component of a video-telephone system. The displayed image can be in the form of an animation sequence whose frames are displayed at a variable frequency dependent on the subject's speech characteristics. Alternatively, conventional graphical representations of biofeedback images such as heart rate, temperature, blood pressure etc. may be displayed on the display monitor 81.

A plurality of sensors 82 are coupled to a control unit 83 having therein a processor (not shown) which controls a multiplexer 84 responsively coupled to the control unit 83 and being connected between the telephone 71 and the telephone line 74. The sensors 82 measure such variables as heart rate, galvanic skin resistance or temperature, known to be influenced by emotional state. The control unit 83 feeds the multiplexer 84 with short bursts representative of the measured physiological variables, these being alternately fed together with the voice data, via the telephone line 74 and the multiplexer 77, to the computer 78 which analyses the speech data.

The speech characteristics representative of the emotion are fed back through the multiplexer 77 to the telephone 73 and, via the telephone line 74, to the multiplexer 84 and the telephone 72 where the data can either be seen visually on the monitor 81 or heard via the speaker in the handle 72. Pre-recorded instructions, scenarios for the feedback audio-visual presentation, and comments are stored in the CD-ROM 79 and the subject's definition and the results of his analysis are stored in the data bank 80.

During most of the time, the telephone unit 72 is connected directly to the telephone line 74. When the digital information representative of the physiological data needs to be transferred, the telephone 72 is disconnected from the telephone line 74 and the processor unit in the control unit 83 is connected thereto via the multiplexer 84.

Figure 3:
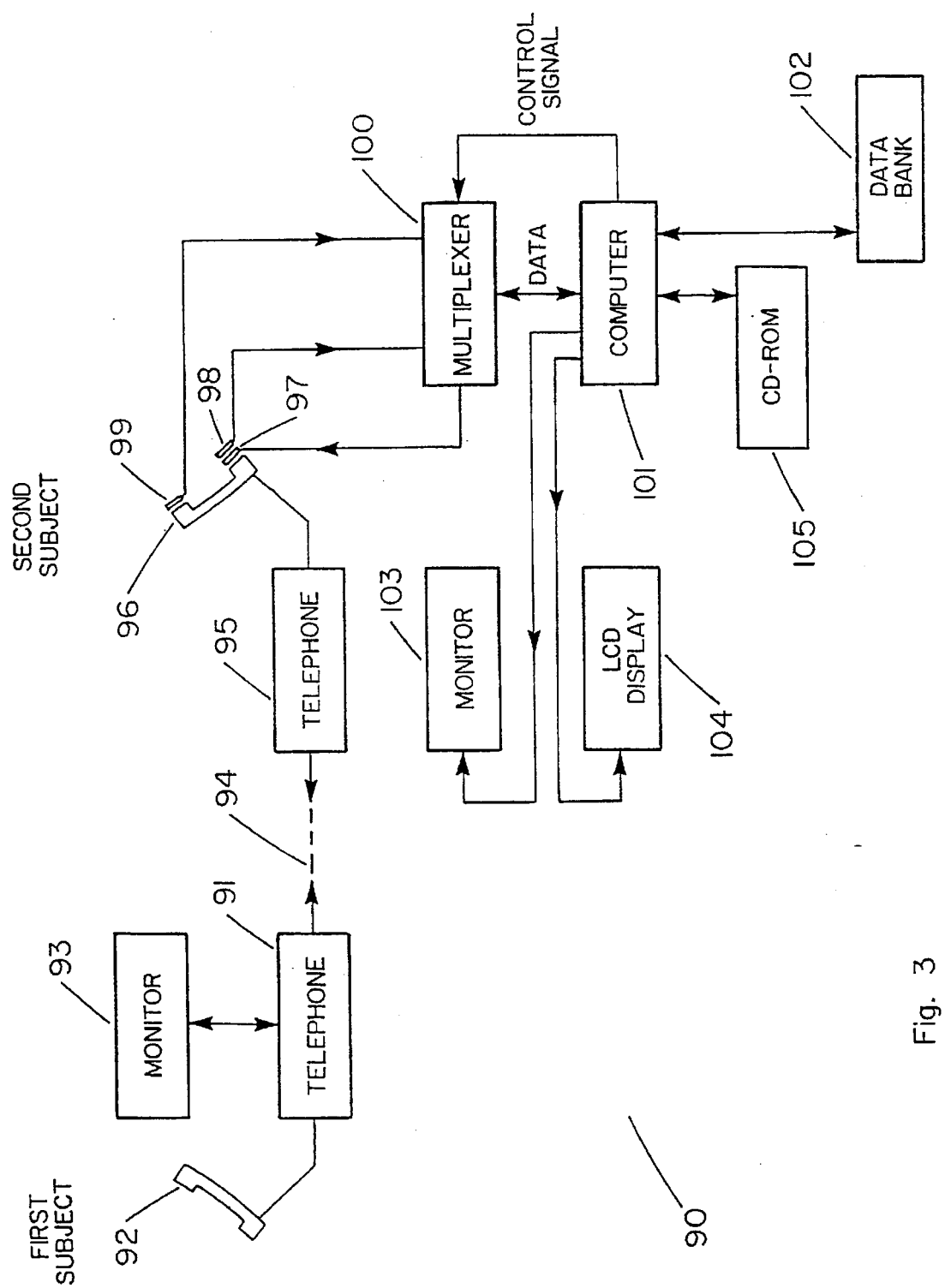
FIG. 3 shows schematically a system used for assessing the emotional state of two subjects conducting a conversation and providing a feedback signal to each subject.

FIG. 3 shows schematically a system 90 used during a conversation between two subjects whereby the emotions of both subjects and feedback signals can be presented to one or both of the subjects. The system 90 can be installed on existing telephone systems without needing special permission by the telephone company. The system 90 comprises a telephone 91 having a handle 92 and being connected to a display monitor 93. The telephone 91 is connected, via a telephone line 94, to a remote telephone 95 provided with a handle 96. The handle 96 includes therein a conventional mouthpiece and earpiece (not shown). An auxiliary speaker 97 and first microphone 98 are fitted to the mouthpiece and a second auxiliary microphone 99 is fitted to the earpiece within the handle 96. The auxiliary speaker and the two auxiliary microphones 98 and 99 are coupled, via a multiplexer 100 to a computer 101 which itself is connected to a data bank 102, a display monitor 103, an LCD display 104 and a CD-ROM 105.

The first subject speaks through the telephone handle 92 of the telephone 91 and his voice is received by the remote telephone 95 and rendered audible through the earpiece contained in the handle 96 thereof so as to be heard by the second subject. At the same time, the second microphone 99 converts the speech signal which is characteristic of the first subject's emotional state and is rendered audible by the earpiece in the handle 96, to a corresponding electrical signal which is fed, via the multiplexer 100, to the computer 101 which analyzes the speech data. The speech characteristics of the first subject are produced in the form of signal bursts having a short time duration and which are fed to the auxiliary speaker 97 and rendered audible thereby. The audible signal bursts are then transmitted via the telephone line 94 to the telephone 91 so as to be audible to the first subject. The monitor 93 is an integral component of the telephone 91, thus permitting the fed back signal to be also presented to the first subject in the form of a visual image as described previously. Likewise, the second subject's voice is fed in conventional manner down the telephone line 94 to the first subject and, at the same time, is conveyed by the first microphone 98 to the computer 101 via the multiplexer 100.

As is known, each subject has a unique template of speech characteristics which permit him to be identified. The features of the speech of the first subject are stored in the data bank 102. The speech of the second subject is detected by the first microphone 98 and conveyed, via the multiplexer 100, to the computer 101. The analyzed speech characteristics are used to generate a feedback signal that can be displayed either on the monitor 103 or on the LCD display 104. The speech characteristics of the second subject are also used to characterize the speaker by a unique template. Thus, when either speaker speaks, the computer 101 identifies the subject and evaluates his emotional states so that the correct fed back signal is transmitted to him.

It should be clear that the second subject might hear the fed back signal sent via microphone 97 to the first subject. If desired, this may be prevented by employing a similar technique as described previously with reference to FIG. 2c so that the second subject does not hear the signal which is fed back to first subject.

It should be noted that the auxiliary speaker 97 and first microphone 99 can be a commercially available integral microphone-speaker units such as are used, for example, in cellular phones.

Figure 4:
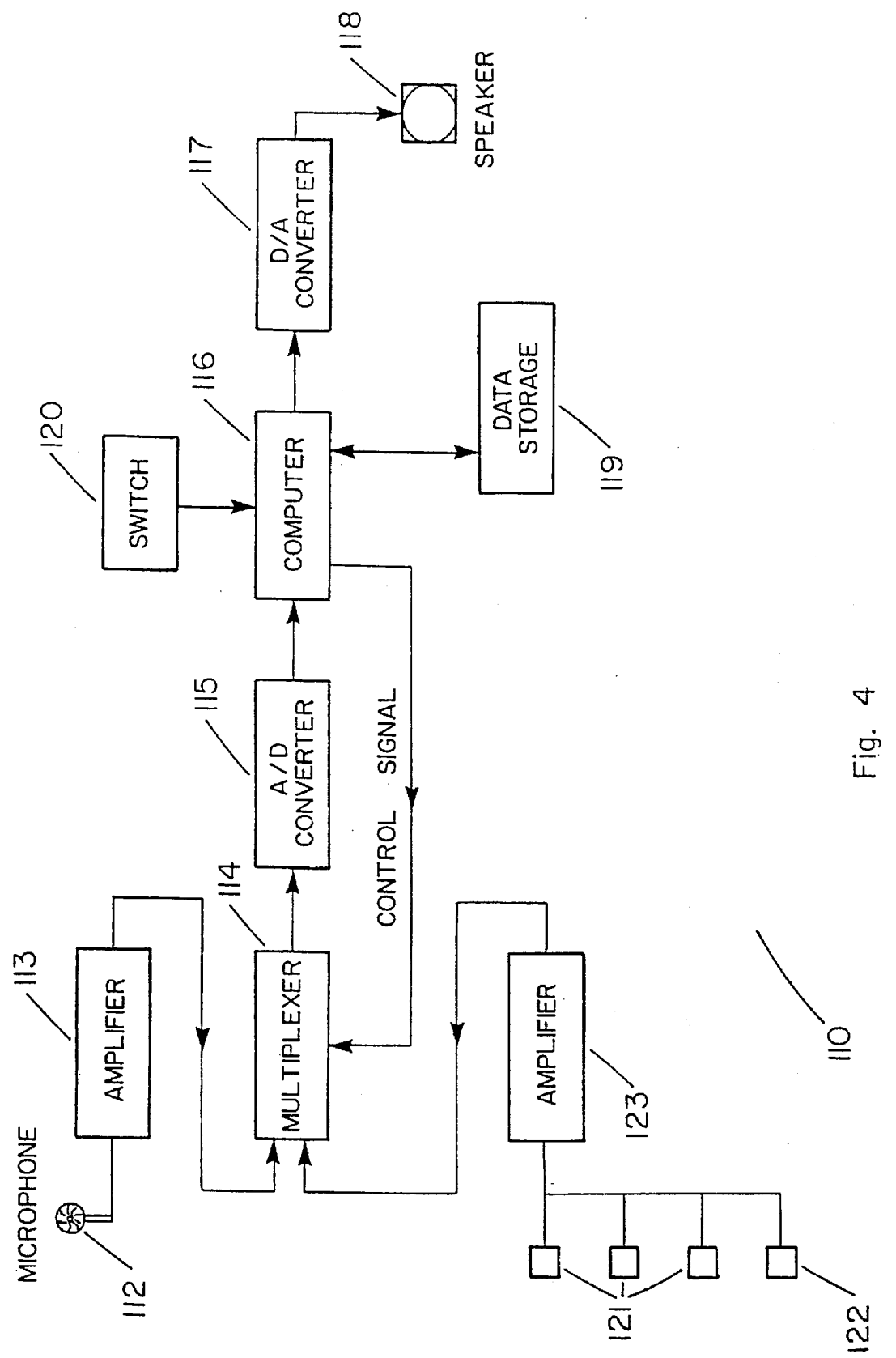
FIG. 4 shows schematically a speech-operated biofeedback system for mounting in a child's toy.

Referring now to FIG. 4 there is shown a block diagram of a system 110 which may be secluded within a child's toy. The system 110 includes a microphone 112 which detects the child's voice and produces a corresponding speech signal which is amplified by an amplifier 113 and fed to a multiplexer 114. An A/D converter 115 is connected to an output of the multiplexer 114 and is, in turn, connected to a computer 116. The computer 116 is coupled, via a D/A converter 117, to a loudspeaker 118, to a storage device 119 for storing therein a set of voice synthesized messages, and to an ON-OFF switch 120. Connected to respective inputs of the multiplexer 114 is a plurality of pressure sensors 121 and a temperature sensor 122, whose outputs are fed to an amplifier 123.

The pressure sensors 121 produce corresponding pressure signals and the temperature sensor 122 produces a signal representative of ambient temperature, these signals being amplified by the amplifier 123 and multiplexed by the multiplexer 114 with the speech signal produced by the microphone 112. The resulting multiplexed signals are digitized by the A/D converter 115, and fed to the computer 116 which analyzes the speech for special characteristics related to emotional reaction. The pre-stored set of messages in the storage device 119 are converted to synthesized speech by the computer 116 and fed via the D/A converter 117 to the loudspeaker 118. A unique template of the child's speech characteristics is stored in the storage device 119 so that the system can identify and separate the speech of different children.

Additionally, the system 110 can detect pressure applied by the child on the toy in which the system is installed by mean of the pressure sensors 121. The repertoire of the pre-stored massages is large and may include such messages as "please don't press me, you are hurting me". Likewise, a suitable message may be enunciated if the ambient temperature detected by the temperature sensor 122, exceeds a pre-set temperature level.

By such means the emotional reaction of the child may be monitored by the toy and self-regulated by biofeedback. If the child is angry, this will be reflected in his voice and the toy can respond "calm down, don't be angry!". Likewise, if the child throws the toy in anger, this will be detected by the pressure sensors 121 and a similar verbal message can be produced.

Figure 5:
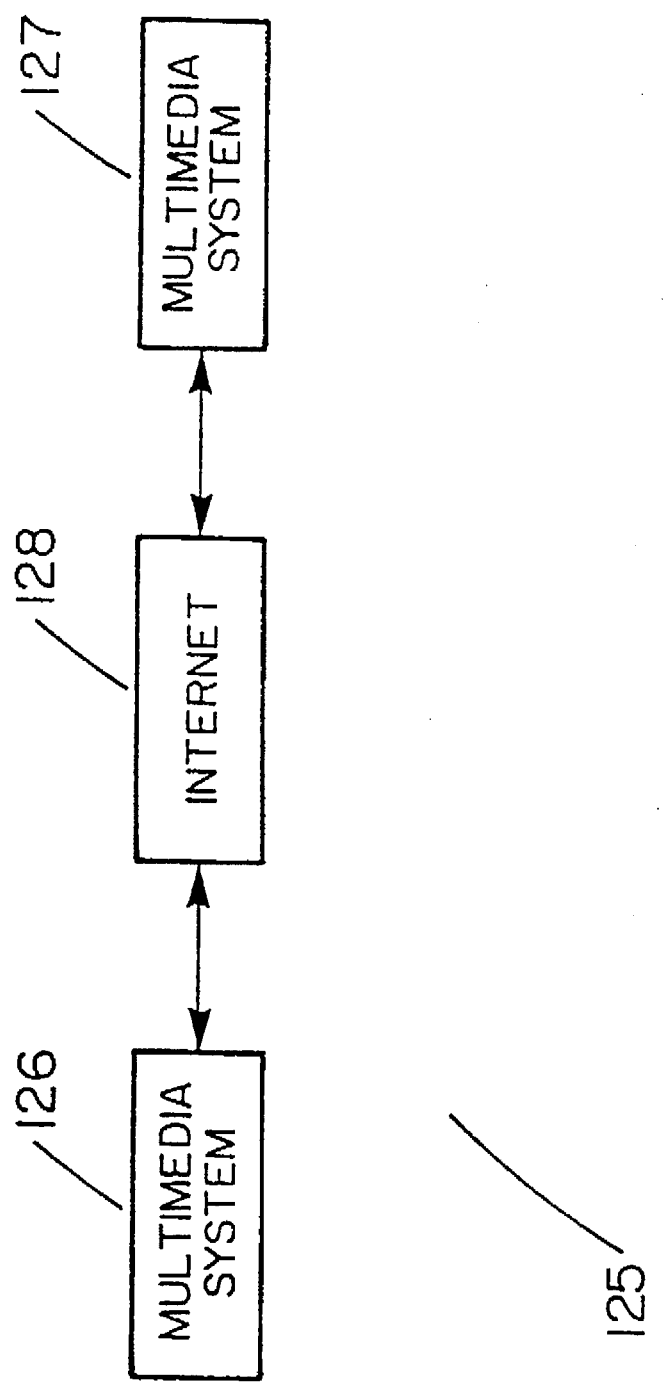
FIG. 5 shows schematically two multimedia systems as shown in FIG. 1 communicating via the Internet.

Referring now to FIG. 5, there is shown a system 125 comprising a pair of multimedia systems 126 and 127 communicating via the Internet, shown schematically as 128. By such means, two subjects can communicate over the telephone line so as to exchange computer files. In this case, the subject's emotional state can be determined locally and encoded within a file which is transferred over the network to the remote party. It is then decoded so as to derive therefrom the subject's emotional state which is the visually or acoustically displayed to the remote party. If desired, the subject's emotional state may be correlated with a look-up table in the CD-ROM 18 (shown in FIG. 1) so as to extract therefrom a suitable textual message such as "the subject is somewhat irritable and tired" which can then be stored in the transfer file. Alternatively, the transfer file can contain in encoded form a vector of the subject's emotional state which is then decoded by the remote party and output as a visual image or audible message.

Figure 6:
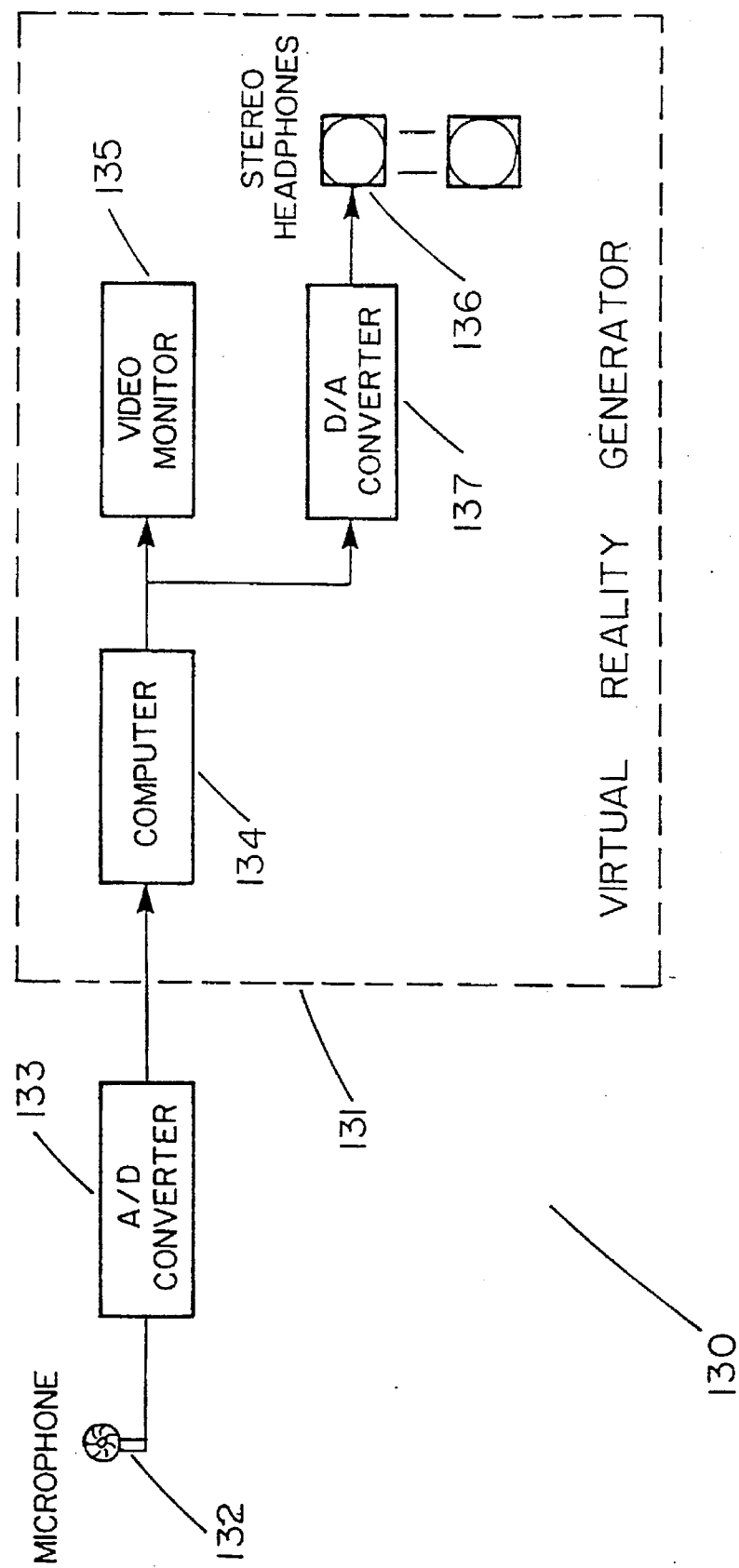
FIG. 6 shows schematically an implementation of the system shown in FIG. 1 for use within a virtual reality system.

FIG. 6 shows an implementation of a system 130 as part of a virtual reality system employed by the subject. The system 130 comprises a virtual reality generator 131 coupled to a microphone 132 via an A/D converter 133 for converting the subject's speech to digital form. The virtual reality generator 131 includes a computer 134 connected to a video monitor 135 and a D/A converter 137 coupled to a pair of stereo headphones 136. The computer 134 analyzes the subject's speech characteristics so as to derive therefrom an indication signal representative of his emotional state. Virtual reality software within the computer 134 is responsive to the indication signal for producing a virtual reality scenario which is viewed and heard by the subject and varies in accordance with the indication signal. For example, if the subject is happy a scenic landscape may be displayed in bright sunny colors with birds singing; whilst if he is angry, a thunderstorm can be produced using sight anal sound effects.

It will be appreciated that changes to the preferred embodiments will be apparent to those skilled in the art, without departing from the spirit of the invention. For example, there may be presented on the display monitor one or more icons whose color varies according to the subject's emotional state as characterized by his voice or other desired physiological variables such as heart rate, skin temperature, skin resistance and so on. Several icons can likewise be used, each representing a different emotion so that the extent to which the subject is happy, relaxed, amused etc. can be seen visually by means of the color of each representative icon. Alternatively, the subject's emotional state can be represented as a message on the screen. In either case, the image can be displayed on the same display device as a computer game so as to indicate the subject's emotional state during the course of the game. For example, the card game "solitaire" can be displayed side by side with an icon representing the subject's emotional state, such that the color of the icon changes when the subject becomes tense or excited, and so on.

Likewise, whilst particular reference to the use of a telephone line is made in the description of the preferred embodiments, it will be readily apparent that any communication channel including wireless communication can be employed.

I claim:

1. A method for effecting biofeedback regulation of at least one physiological variable characteristic of a subject's emotional state, comprising the steps of:
   (a) monitoring at least one speech parameter characteristic of the subject's emotional state so as to produce an indication signal representative of the at least one physiological variable,
   (b) consciously altering the subject's emotional state so as to induce a desired change in the indication signal;
   (c) monitoring at least one non-speech parameter characteristic of the subject's emotional state so as to determine a reference level of said non-speech parameter when the at least one physiological variable is at a required level, and
   consciously altering the at least one speech parameter so as to cause said non-speech parameter to assume said reference level.

2. The method according to claim 1 for training the subject to speak in a manner which does not reflect his emotional state, further comprising the steps of:
   (c) monitoring at least one non-speech parameter characteristic of the subject's emotional state so as to determine a reference level of said non-speech parameter when the at least one physiological variable is at a required level, and
   (d) consciously altering the at least one speech parameter so as to cause said non-speech parameter to assume a different level to said reference level.

3. The method according to claim 1, wherein said indication signal is a pre-recorded audio-visual scenario whose content changes according to the subject's emotional state.

4. The method according to claim 3, wherein the subject selects a desired audio-visual scenario according to a required emotion that is to be exposed.

5. The method according to claim 3, wherein the audio-visual scenario is a game having an objective which is achieved only when the subject reaches a required emotional state.

6. The method according to claim 3, wherein the audio-visual scenario changes at a rate dependent on the subject's emotional state.

7. The method according to claim 3, wherein the subject selects a desired visual image according to a required emotion that is to be exposed.

8. The method according to claim 3, wherein the subject selects desired auditory sounds according to a required emotion that is to be exposed.

9. The method according to claim 1, wherein the indication signal is derived at a location remote from the subject.

10. The method according to claim 9, wherein the subject is fed the indication signal via a communication channel.

11. The method according to claim 10, wherein the subject communicates with a remote party via the communication channel and the indication signal is not fed to the remote party.

12. The method according to claim 11, wherein the subject transfers to the remote party via the communication channel a file encoding therein his emotional state which is decoded by the remote party so as to derive therefrom the subject's emotional state which is then visually or audibly output by the remote party.

13. The method according to claim 10, wherein the subject communicates with a remote party via the communication channel and the indication signal is fed to the remote party.

14. The method according to claim 13, wherein the subject transfers to the remote party via the communication channel a file encoding therein his emotional state which is decoded by the remote party so as to derive therefrom the subject's emotional state.

15. The method according to claim 1, wherein said indication signal is a set of icons each corresponding to a respective emotional state.

16. The method according to claim 1, wherein the subject is hearing-impaired and the indication signal is not audible.

17. The method according to claim 1, wherein the subject is unable to express himself emotionally and the indication signal is indicative of a broad category of emotional state.

18. The method according to claim 1, for quantitatively assessing an alertness level of the subject relative to an initial extreme state of tiredness or alertness, further comprising the steps of:
   (c) deriving a reference indication signal when the subject is at said extreme state of tiredness or alertness and storing data representative of the reference indication signal,
   (d) deriving the indication signal when it is required to assess the subject's alertness level and comparing data representative of the indication signal with said stored data so as to derive a difference signal which provides a quantitative assessment of the subject's relative alertness to said extreme state.

19. A system for effecting biofeedback regulation of at least one physiological variable characteristic of a subject's emotional state, the system comprising:
   a microphone for converting the subject's speech to an electrical signal,
   a processing means coupled to the microphone for deriving from the electrical signal at least one speech parameter characteristic of the subject's emotional state and for producing therefrom an indication signal,
   an indication means coupled to the processing means and responsive to the indication signal for providing the subject with an indication of the at least one physiological variable;
   at least one sensor for detecting a non-speech parameter characteristic of the subject's emotional state and producing a corresponding sensor signal, and
   reference signal means coupled to the at least one sensor and responsive to the sensor signal for determining a reference level of said non-speech parameter when the at least one physiological variable is at a required level.

20. The system according to claim 19, wherein the indication means includes voice synthesizing means for producing a verbal indication of the at least one physiological variable.

21. The system according to claim 19, wherein the indication means is a display device for displaying visually said indication of the at least one physiological variable.

22. The system according to claim 19, further including a storage means coupled to the processing means for storing therein a pre-recorded audio-visual scenario;

the indication means being responsive to the indication signal for displaying different frames of said scenario according to the subject's emotional state.

23. The system according to claim 22, further including a selection means coupled to the storage device for selecting a desired audio-visual scenario according to a required emotion that is to be exposed.

24. The system according to claim 22, wherein the audio-visual scenario is a game having an objective which is achieved only when the subject reaches a required emotional state.

25. The system according to claim 22, wherein the audio-visual scenario changes at a rate dependent on the subject's emotional state.

26. The system according to claim 22, further including a selection means coupled to the storage device for selecting a desired visual image according to a required emotion that is to be exposed.

27. The system according to claim 22, further including a selection means coupled to the storage device for selecting desired auditory sounds according to a required emotion that is to be exposed.

28. The system according to claim 19, being a suitably programmed multimedia system.

29. The system according to claim 19, further including:

a virtual reality generator for producing a virtual reality scenario and which is responsively coupled to the indication signal for modifying the virtual reality scenario in accordance with the subject's emotional state.

30. The system according to claim 19 being contained within a child's toy, said indication means including voice synthesizing means for producing a verbal indication of the at least one physiological variable.

31. The system according to claim 30, wherein:

the toy further includes at least one pressure sensor for sensing pressure applied to the toy consequent to a child's emotional state and producing a corresponding pressure signal, and the voice synthesizing means are coupled to the at least one pressure sensor for producing a verbal indication of the child's emotional state.

32. The system according to claim 19, further including a communication channel for conveying the indication signal to a remote party.

33. The system according to claim 32, wherein the microphone is contained within a telephone connected to a communication channel and the biofeedback signal is sent to the subject via the communication channel.

34. The system according to claim 32, further including a remote telephone connected to the communication channel remote from the subject for receiving the indication signal as a tone burst and for allowing the subject to converse with a remote party.

35. The system according to claim 34, further including a filtering means coupled to the remote telephone for preventing the subject from hearing the tone burst.

36. The system according to claim 35, wherein the filtering means is a multiplexer.

37. A method for effecting biofeedback regulation of at least one physiological variable characteristic of a subject's emotional state, comprising the steps of:

(a) simultaneously monitoring a plurality of speech parameters having a combined response which is characteristic of the subject's emotional state and having associated therewith a reference threshold corresponding to a reference emotional state of the subject, (b) determining the reference threshold for the subject, (c) comparing an instantaneous value of the combined response of each of the monitored speech parameters with the corresponding reference threshold so as to produce an indication signal representative of the at least one physiological variable, and (d) consciously altering the subject's emotional state so as to induce a desired change in the indication signal.

38. The method according to claim 37 further including the steps of:

monitoring at least one non-speech based physiological variable, and deriving a combined indication signal based on the monitored speech-based physiological variables and the at least one non-speech based physiological variable.

39. A system for effecting biofeedback regulation of at least one physiological variable characteristic of a subject's emotional state, the system comprising:

a microphone for converting the subject's speech to an electrical signal, a processing means coupled to the microphone for deriving from the electrical signal a plurality of speech parameters each having a combined response which is characteristic of the subject's emotional state and having associated therewith a reference threshold corresponding to a reference emotional state of the subject;

said processing means further:

(a) determining the reference threshold for the subject, and (b) comparing an instantaneous value of the combined response of each of the monitored speech parameters with the corresponding reference threshold so as to produce therefrom an indication signal, and an indication means coupled to the processing means and responsive to the indication signal for providing the subject with an indication of the at least one physiological variable.

* * * * *